(12) United States Patent
Kim et al.

(10) Patent No.: US 10,401,505 B2
(45) Date of Patent: Sep. 3, 2019

(54) OCULAR DOSIMETER AND MANUFACTURING METHOD THEREFOR

(71) Applicant: SEOUL NATIONAL UNIVERSITY HOSPITAL, Seoul (KR)

(72) Inventors: Jung In Kim, Seoul (KR); Jong Min Park, Seoul (KR); Won Mo Sung, Seoul (KR); Hong Gyun Wu, Seoul (KR)

(73) Assignee: SEOUL NATIONAL UNIVERSITY HOSPITAL, Seoul (KR)

( * ) Notice: Subject to any disclaimer, the term of this patent is extended or adjusted under 35 U.S.C. 154(b) by 0 days.

(21) Appl. No.: 16/162,490

(22) Filed: Oct. 17, 2018

(65) Prior Publication Data
US 2019/0086556 A1    Mar. 21, 2019

Related U.S. Application Data

(63) Continuation of application No. PCT/KR2016/015101, filed on Dec. 22, 2016.

(51) Int. Cl.
| | | |
|---|---|---|
| *G01T 1/06* | (2006.01) | |
| *G02C 7/04* | (2006.01) | |
| *A61B 6/00* | (2006.01) | |

(52) U.S. Cl.
CPC .................. *G01T 1/06* (2013.01); *A61B 6/00* (2013.01); *G02C 7/04* (2013.01)

(58) Field of Classification Search
CPC ..... G01T 1/02; G01T 1/04; G01T 1/06; A61B 6/00
See application file for complete search history.

(56) References Cited

U.S. PATENT DOCUMENTS

| | | |
|---|---|---|
| 4,904,421 A | 2/1990 | Ando et al. |
| 8,979,260 B1 | 3/2015 | Keshishian |
| 2005/0024583 A1 | 2/2005 | Neuberger |

FOREIGN PATENT DOCUMENTS

| | | | |
|---|---|---|---|
| JP | 2001517324 A | 10/2001 | |
| WO | 2015107179 A1 | 7/2015 | |
| WO | WO-2015107179 A1 * | 7/2015 | ............... G01T 1/02 |

OTHER PUBLICATIONS

International Search Report dated Aug. 14, 2017.

* cited by examiner

*Primary Examiner* — Michael C Bryant
(74) *Attorney, Agent, or Firm* — Dinsmore & Shohl LLP; Yongsok Choi, Esq.

(57) ABSTRACT

The present disclosure relates to a contact lens type dosimeter for measuring a dose distribution of a crystalline lens during radiation therapy, and a method of manufacturing the same. The ocular dosimeter has a contact lens shape and is configured to be worn on an eyeball, which comprises a basic material containing hydrophilic polyurethane, and a radiochromic dye. When the ocular dosimeter is worn on the eyeball, the dosimeter is configured to measure a radiation dose irradiated to a crystalline lens through a variation in color of the ocular dosimeter.

3 Claims, 3 Drawing Sheets

ОCULAR DOSIMETER AND
MANUFACTURING METHOD THEREFOR

CROSS-REFERENCE TO RELATED
APPLICATIONS

This application is a continuation of PCT/KR2016/015101 filed on Dec. 22, 2016, the entire contents of which are herein incorporated by reference.

FIELD OF THE INVENTION

The present disclosure relates to an ocular dosimeter and a manufacturing method for the same, and more particularly, to a contact lens type dosimeter for measuring a dose distribution of a crystalline lens during radiation therapy, and a manufacturing method for the same.

BACKGROUND

In addition to surgery and chemotherapy, radiation therapy is one of the three major cancer treatment methods, and it is a treatment method of killing cancer cells by irradiating radiation to a tumor volume. Generally, radiotherapy is performed by treating a tumor using ionizing radiation generated from a medical linear accelerator according to diagnosis using medical imaging devices such as a computerized tomography (CT) device, a magnetic resonance imaging (MRI) device, a positron emission tomography (PET), and the like.

In the course of radiotherapy, when radiation is delivered to the tumor volume, normal organs around the tumor volume may also be exposed to radiation. Thus, in radiotherapy, it is important to minimize radiation delivery to the normal organs around the tumor volume while delivering radiation sufficient to kill cancer cells in the tumor volume.

As radiation therapy techniques for improving accuracy and minimizing side effects, an intensity modulated radiation therapy (IMRT) technique, an image guided radiation therapy (IGRT) technique, an adaptive radiation therapy (ART) technique, and the like are known, and these techniques are continuously being developed on the basis of convergence technology. Owing to the development of these radiation therapy techniques and the complexity of a treatment planning system used for a radiation treatment plan, it is necessary to measure and verify an actual radiation dose, and to this end, various dosimeters have been developed.

Meanwhile, even in the case of head and neck radiotherapy, the surrounding organs may be generally exposed to radiation, and particularly, among the surrounding organs exposed to such radiation, a crystalline lens is one of the most sensitive organs to radiation. When a dose, which exceeds about 15% of a usual treatment prescribed dose during head and neck radiotherapy, is delivered to the crystalline lens, severe side effects such as amblyopia and a cataract may occur.

In order to minimize such side effects, it is necessarily required for a bio-dosimeter capable of measuring a dose being irradiated to a crystalline lens.

As of now, however, it is only possible to indirectly evaluate a does inside a crystalline lens by attaching a dosimeter capable of measuring a dot dose to a periphery surface of an eyeball, so that it is required to develop a technique capable of accurately measuring a dose distribution of the crystalline lens.

SUMMARY OF THE INVENTION

Therefore, it is an object of the present disclosure to provide an ocular dosimeter capable of accurately measuring a dose distribution of a crystalline lens during radiotherapy and a method of manufacturing the same.

According to one aspect of the present disclosure, there is provided an ocular dosimeter having a contact lens shape and capable of being worn on an eyeball, which comprises a basic material containing hydrophilic polyurethane, and a radiochromic dye, wherein, when the ocular dosimeter is worn on the eyeball, the dosimeter is capable of measuring a radiation dose irradiated to a crystalline lens through a variation in color of the ocular dosimeter.

The radiochromic dye may comprise leucomalachite green (LMG).

The basic material containing hydrophilic polyurethane may comprise hydroxyethyl methacrylate (HEMA) and $CBr_4$.

According to another aspect of the present disclosure, there is provided a method of manufacturing an ocular dosimeter, which comprises preparing hydrophilic polyurethane in a first container, adding and dissolving $CBr_4$ in the first container, adding and dissolving a radiochromic dye in the first container, preparing mixture liquid of hydrophilic polyurethane to which hydroxyethyl methacrylate (HEMA) is added in a second container different from the first container, mixing the mixture liquid of the first container with the mixture liquid of the second container and injecting the mixture into a female mold for a contact lens molding, covering the female mold with a male mold, molding the mixture in a form of a contact lens into, and curing the molding, and cleaning the cured molding in the form of a contact lens.

The radiochromic dye may comprise a leucomalachite green (LMG).

2% LMG may be added to hydrophilic polyurethane in the first container.

1% $CBr_4$ may be added to hydrophilic polyurethane in the first container.

5% HEMA may be added to hydrophilic polyurethane in the second container.

In accordance with one embodiment of the present disclosure, an ocular dosimeter is formed in a contact lens shape containing a radiochromic dye, such that a three-dimensional dose distribution of a crystalline lens can be accurately and rapidly measured through variation in color of a lens during radiotherapy.

Figure 1:
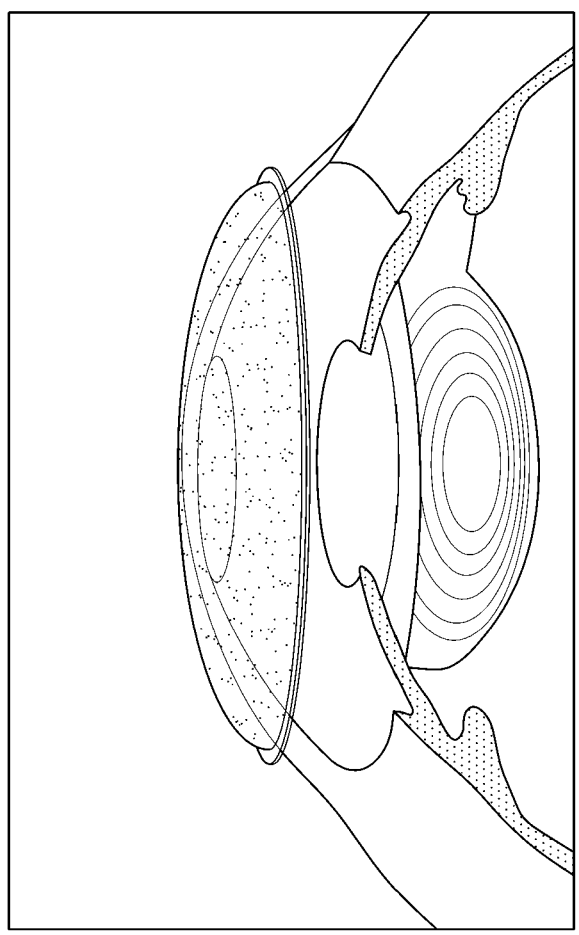
FIG. 1 is a diagram illustrating a case of using an ocular dosimeter according to the present disclosure.

DETAILED DESCRIPTION OF THE
PREFERRED EMBODIMENTS

Hereinafter, preferred embodiments of the present disclosure will be fully described in a detail which is suitable for implementation by those skilled in the art to which the present disclosure pertains with reference to the accompanying drawings.

In order to clearly describe the present disclosure, a portion not related to the present disclosure will be omitted, and throughout this disclosure, like reference numerals will be assigned to like components. Further, a size and the like of each element shown in the drawings are arbitrarily illustrated for convenience of description, and thus the present disclosure is not necessarily limited to those shown in the drawings.

That is, it should be noted that specific shapes, structures, and features described herein can be changed and implemented from one embodiment to another embodiment without departing from the spirit and scope of the present disclosure, and a position or an arrangement of each element can also be changed without departing from the spirit and scope of the present disclosure. Accordingly, the following detailed description is not to be taken in a limiting sense, and the scope of the present disclosure should be construed to include the scope of the appended claims and equivalents thereof.

Shape of Ocular Dosimeter

FIG. 1 is a diagram illustrating a case of using an ocular dosimeter according to the present disclosure. Referring to FIG. 1, the ocular dosimeter according to the present disclosure is made of a contact lens type, specifically, a soft contact lens type.

Accordingly, when there is radiation exposure such as radiotherapy, the ocular dosimeter of the present disclosure is capable of directly measuring a dose distribution of a crystalline lens by being directly worn and used on an eyeball.

Hereinafter, a material and a manufacturing method of a contact lens type ocular dosimeter will be described in detail.

Material for Ocular Dosimeter

Generally, a contact lens being directly worn on an eyeball, which is a sensitive body part, is required to have high safety and an excellent wearing feeling while being used. For example, when a contact lens is worn, there should be no feeling of irritation and no pressure on the cornea. Further, when the contact lens is manufactured, it should consider many factors such as oxygen transmissibility, a water content, biocompatibility, and the like of the contact lens.

In one embodiment of the present disclosure, when a contact lens type ocular dosimeter is fabricated, a material satisfying the above-described requirements is basically used and a material for detecting radiation is further used.

As a basic material of the contact lens type ocular dosimeter, mixture liquid of hydrophilic polyurethane and the like is used, and hydroxyethyl methacrylate (HEMA), tetrabromomethane ($CBr_4$), and the like are used as material mixed with hydrophilic polyurethane.

Polyurethane used in the present embodiment may have an optically transparent property and a low viscosity, thereby being smoothly mixed and poured together with other materials. When being cured at room temperature, polyurethane is hardly contracted and is not vulnerable to cracking after being cured.

HEMA is an acrylic monomer of a simplified structure having a small number of carbon atoms and has a polymeric vinyl group while sharing a hydroxyl group and a carboxyl group, and thus HEMA is widely used to produce an optically active biopolymer and, specifically, is mainly used as a basic material for a soft contact lens. Further, $CBr_4$ serves to improve moldability and curability when molded in the form of a contact lens.

Such materials are used as basic materials, so that it is possible not only to allow the material of the contact lens type ocular dosimeter to be soft, but also to reduce a feeling of irritation and reduce a pressure on the cornea when the contact lens type ocular dosimeter is worn.

In the present disclosure, a radiochromic dye is used together with the above-described materials so as to measure a three-dimensional dose distribution of a crystalline lens through the contact lens type ocular dosimeter.

The radiochromic dye is a material of which color is changed caused by modification of a structural formula when undergone radiation exposure, and in one embodiment of the present disclosure, leucomalachite green (LMG) is used as such a radiochromic dye.

When radiation is irradiated, LMG is changed to a malachite green cation ($MG^+$) to exhibit a green color, and an amount of $MG^+$ is proportional to an irradiated radiation dose. Therefore, it is possible to detect the irradiated radiation dose according to the amount of MG+. That is, when the contact lens type ocular dosimeter is worn on an eyeball, the degree of radiation exposure of the crystalline lens may be measured according to a variation in color of the contact lens type ocular dosimeter.

As such, the above-described materials are used in the present embodiment, and thus the contact lens type ocular dosimeter may be directly worn on an eyeball to directly measure a radiation dose irradiated to the crystalline lens through a variation in color of the contact lens type ocular dosimeter.

Method of Manufacturing Ocular Dosimeter

Figure 2:
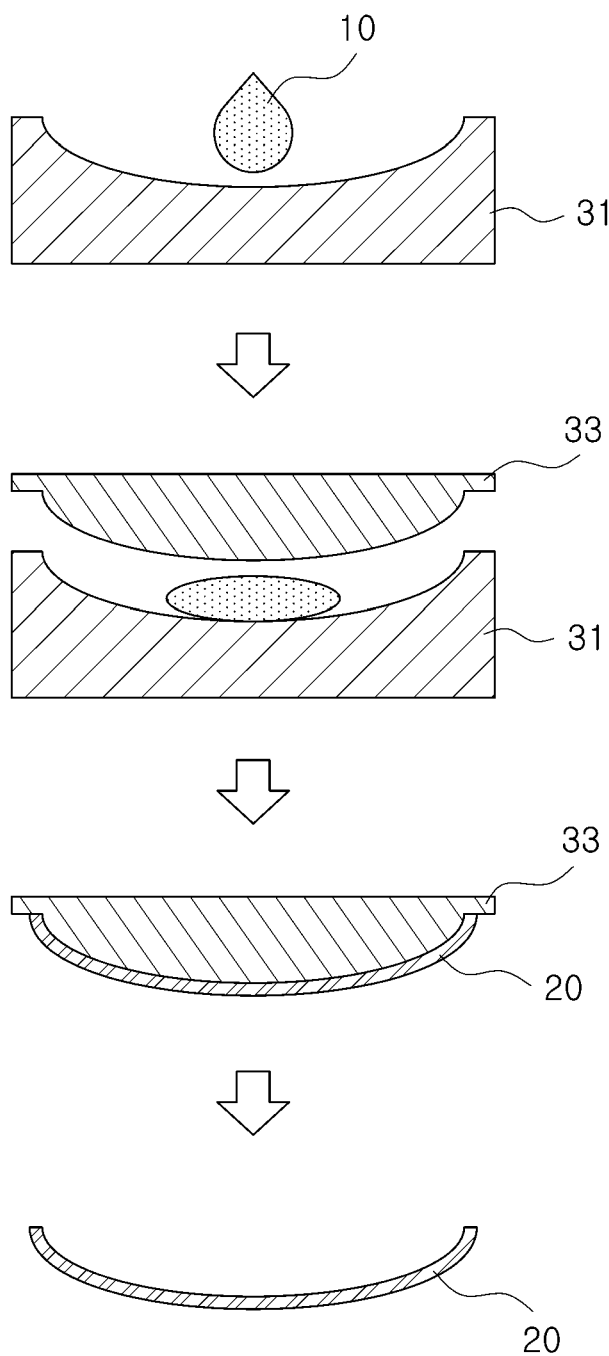
FIG. 2 is a diagram schematically illustrating a process of manufacturing the ocular dosimeter according to one embodiment of the present disclosure.
Figure 3:
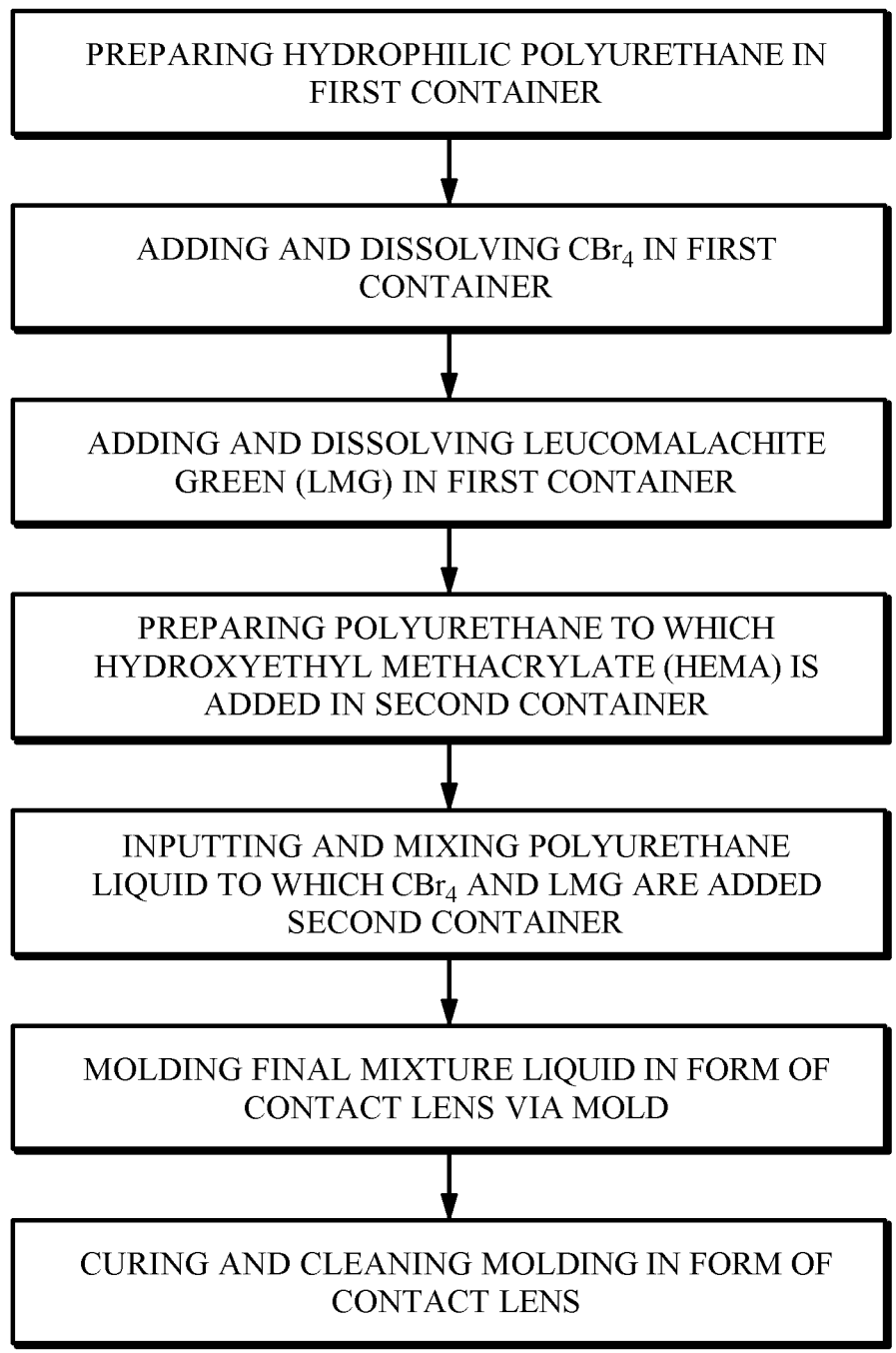
FIG. 3 is a flowchart sequentially illustrating the process of manufacturing the ocular dosimeter according to one embodiment of the present disclosure.

FIG. 2 is a diagram schematically illustrating a process of manufacturing the ocular dosimeter according to one embodiment of the present disclosure, and FIG. 3 is a flowchart sequentially illustrating the process of manufacturing the ocular dosimeter according to one embodiment of the present disclosure. Hereinafter, a method of manufacturing an ocular dosimeter according to the present disclosure will be described together with specific examples with reference to FIGS. 2 and 3.

In the present disclosure, as shown in FIG. 2, a contact lens type ocular dosimeter is manufactured through a molding method using a cast mold.

First, mixture liquid for manufacturing an ocular dosimeter through a cast mold is produced.

Referring to FIG. 3, hydrophilic polyurethane is first prepared in a first container. Next, $CBr_4$ is added to the first container accommodating hydrophilic polyurethane to be dissolved. Then, a radiochromic dye is added to the first container to be dissolved.

In the present embodiment, a product of Crystal Clear series produced by Smooth-On Incorporation was used as hydrophilic polyurethane, and Part-B was used for the first container.

Further, in the present embodiment, LMG is used as the radiochromic dye, and a process of adding and dissolving LMG to the first container proceeds by minimizing light exposure.

In mixing hydrophilic polyurethane (Part-B), $CBr_4$, and LMG in the first container, $CBr_4$ having a concentration of 1% and LMG having a concentration of 2% are used with, and weight ratios of hydrophilic polyurethane (Part-B), $CBr_4$, and LMG are approximately 45:1:2. However, the present disclosure is not limited to the above-described concentration of each material and the above-described mixed weight ratio thereof, and in some cases, it is possible to adjust a concentration and a mixed weight ratio of each material.

A sonicator is used when $CBr_4$ and LMG are added and dissolved. However, the present disclosure is not limited thereto, and it is possible to dissolve $CBr_4$ and LMG through any other known method.

In addition to preparing the mixture liquid of hydrophilic polyurethane (Part-B), $CBr_4$, and LMG in the first container, hydrophilic polyurethane to which HEMA is added is prepared in a second container.

Part-A among Crystal Clear series products produced by Smooth-On Incorporation is used as hydrophilic polyurethane prepared in the second container, and a weight ratio of Part-A prepared in the second container to Part-B prepared in the first container was about 10:9.

In the present embodiment, 5% HEMA is added to hydrophilic polyurethane (Part-A) of the second container, and a weight ratio of HEMA to hydrophilic polyurethane (Part-A) is approximately 1:9. However, concentrations and mixed weight ratios of such materials may also be adjusted.

For example, when the mixture liquid is prepared in each of the first container and the second container, the mixture liquid of the first container is mixed with the mixture liquid in the second container by pouring the mixture liquid of the first container into the second container. At this point, the mixtures are evenly stirred while preventing generation of bubbles.

The mixture liquid prepared through the above-described process becomes final mixture liquid for manufacturing an ocular dosimeter.

Referring to FIG. 2, final mixture liquid 10 is injected into a female mold 31 of cast molds prepared in advance for form a contact lens shape. Thereafter, in order to spread the final mixture liquid 10 in a desired contact lens shape, a male mold 33 covers the female mold 31, wherein the male mold 33 matches the female mold 31.

The male mold 33 and the female mold 31 are coupled to maintain the contact lens shape and the final mixture liquid 10 are cured for a long period of time. In the present embodiment, the curing of the final mixture liquid 10 is performed under a dark room condition at room temperature, but the present disclosure is not necessarily limited thereto.

When completely cured, a contact lens type molding 20 is separated from the female and male molds 31 and 33 and cleaned with physiological saline or the like.

Manufacturing of the contact lens type ocular dosimeter is completed through the above-described process.

The contact lens type ocular dosimeter manufactured as described above may include a radiochromic dye to measure a radiation dose through a variation in color when exposed to radiation. Therefore, during radiotherapy, specifically, head and neck radiotherapy, a patient wears the contact lens type ocular dosimeter on an eyeball, so that it is possible to directly measure a radiation dose irradiated to a crystalline lens, i.e., a three-dimensional dose distribution of the crystalline lens, such that amblyopia, a cataract, and the like which are caused by radiation exposure can be prevented in advance.

Further, in the present embodiment, a suitable material is used in manufacturing an ocular dosimeter, such that it is possible to satisfy requirements such as a feeling of wearing, safety, oxygen permeability, water content, biocompatibility, and the like which are required for manufacturing the ocular dosimeter in the form of a contact lens.

While the exemplary embodiments of the present disclosure have been described with reference to the accompanying drawings, those skilled in the art to which the present disclosure pertains can understand that the present disclosure can be implemented in other specific forms without departing from the technical spirit or the necessary features of the present disclosure. Therefore, it should be understood that the above-described embodiments are not restrictive but illustrative in all aspects.

What is claimed is:

1. An ocular dosimeter having a contact lens shape and configured to be worn on an eyeball, the ocular dosimeter comprising:
   a basic material containing hydrophilic polyurethane; and
   a radiochromic dye,
   wherein, when the ocular dosimeter is worn on the eyeball, the ocular dosimeter is configured to measure a radiation dose irradiated to a crystalline lens through a variation in color of the ocular dosimeter.

2. The ocular dosimeter of claim 1, wherein the radiochromic dye comprises leucomalachite green (LMG).

3. The ocular dosimeter of claim 1, wherein the basic material containing hydrophilic polyurethane comprises hydroxyethyl methacrylate (HEMA) and $CBr_4$.

* * * * *